United States Patent
Karembe et al.

(10) Patent No.: US 11,134,685 B2
(45) Date of Patent: Oct. 5, 2021

(54) COMPOSITIONS AND USES THEREOF FOR CONTROLLING ECTOPARASITES IN NON-HUMAN MAMMALS

(71) Applicant: Ceva Santé Animale, Libourne (FR)

(72) Inventors: Hamadi Karembe, Libourne (FR); Marie Varloud, Libourne (FR)

(73) Assignee: Ceva Santé Animale, Libourne (FR)

( * ) Notice: Subject to any disclaimer, the term of this patent is extended or adjusted under 35 U.S.C. 154(b) by 0 days.

(21) Appl. No.: 16/776,303

(22) Filed: Jan. 29, 2020

(65) Prior Publication Data
US 2020/0163339 A1    May 28, 2020

Related U.S. Application Data

(62) Division of application No. 15/747,374, filed as application No. PCT/EP2016/067561 on Jul. 22, 2016, now abandoned.

(30) Foreign Application Priority Data

Jul. 24, 2015   (EP) .................................... 15306211

(51) Int. Cl.
| | | |
|---|---|---|
| *A01N 51/00* | (2006.01) | |
| *A61K 31/341* | (2006.01) | |
| *A61K 31/415* | (2006.01) | |
| *A01N 47/02* | (2006.01) | |

(52) U.S. Cl.
CPC ............. *A01N 51/00* (2013.01); *A01N 47/02* (2013.01); *A61K 31/341* (2013.01); *A61K 31/415* (2013.01)

(58) Field of Classification Search
CPC .............. A61K 2300/00; A61K 31/341; A61K 31/415; A01N 47/02; A01N 51/00; A61P 33/14
See application file for complete search history.

(56) References Cited

U.S. PATENT DOCUMENTS

| | | | | |
|---|---|---|---|---|
| 7,368,435 B2 * | 5/2008 | Cottrell | ................... | A61P 33/10 514/30 |
| 2006/0105009 A1 | 5/2006 | Bregante | | |
| 2008/0009452 A1 | 1/2008 | Barazani et al. | | |
| 2008/0194642 A1 * | 8/2008 | Albright | ................ | A01N 47/34 514/341 |
| 2011/0092560 A1 * | 4/2011 | Del Bigio | .............. | A61K 47/10 514/407 |
| 2012/0071484 A1 | 3/2012 | Reynolds | | |
| 2012/0255502 A1 * | 10/2012 | Holmes | ................... | A61P 33/00 119/651 |
| 2013/0225516 A1 | 8/2013 | Soll et al. | | |
| 2017/0136080 A1 | 5/2017 | Guimberteau et al. | | |
| 2018/0213790 A1 | 8/2018 | Karembe et al. | | |
| 2018/0235926 A1 | 8/2018 | Varloud et al. | | |

FOREIGN PATENT DOCUMENTS

| | | |
|---|---|---|
| EP | 0 295 117 A1 | 12/1988 |
| EP | 0 649 845 A1 | 4/1995 |
| WO | WO 2005/015995 A1 | 2/2005 |
| WO | WO 2006/039079 A2 | 4/2006 |
| WO | WO 2007/143298 A2 | 12/2007 |
| WO | WO 2009/027506 A2 | 3/2009 |
| WO | WO 2010/109214 A2 | 9/2010 |
| WO | WO2012107585 A1 * | 8/2012 |
| WO | WO 2013/152315 A1 | 10/2013 |

OTHER PUBLICATIONS

Guimberteau, English translation of WO2012107585, 2012 (Year: 2012).*
Diaz et al., "Introduction to Ectoparasitic Diseases" in Mandell, Douglas, and Bennett's Principles and Practice of Infectious Disease (Eight Edition), vol. 2, 2015 (Year: 2015).*
International Search Report and Written Opinion dated Oct. 12, 2016 for Application PCT/EP2016/067561.
International Preliminary Report on Patentability dated Feb. 8, 2018 for Application PCT/EP2016/067561.
[No Author Listed], SVP7 EPA Label Amendment, EPA Registration No. 83399-6. United States Environmental Protection Agency, Office of Chemical Safety and Pollution Prevention. Feb. 2, 2014. 16 pges.
[No Author Listed], VECTRA 3D: Annex I Summary of Product Characteristics. Jan. 1, 2013. Last accessed from http://ec.europa.eu/health/documents/community-register/2013/20131204127161/anx_127161_en.pdf on Sep. 15, 2016. 25 pages.
Hoch et al., Canine and feline dirofilariasis: life cycle, pathophysiology, and diagnosis. Compend Contin Educ Vet. Mar. 2008;30(3):133-40; quiz 141.
Hoch et al., Canine and feline dirofilariasis: prophylaxis, treatment, and complications of treatment. Compend Contin Educ Vet. Mar. 2008;30(3):146-51; quiz 151-2.
Leonardi, Vectra 3D for dogs—Flea Med Precautions and Use. Sep. 25, 2013. Last accessed from https://www.petcarerx.com/article/vectra-3d-for-dogs-flea-med-precautions-and-use/1366 on Dec. 3, 2015. 8 pages.
Testa et al., Predicting drug metabolism: Concepts and challenges. Pure Appl. Chem. 2004;76(5):907-914.
McCall, The safety-net story about macrocyclic lactone heartworm preventives: a review, an update, and recommendations. Vet Parasitol. Oct. 24, 2005;133(2-3):197-206. doi: 10.1016/j.vetpar.2005.04.005. Epub Apr. 26, 2005.
Bourguinat et al., Macrocyclic lactone resistance in Dirofilaria immitis Vet Parasitol. Sep. 27, 2011;181(2-4):388-92. doi: 10.1016/j.vetpar.2011.04.012. Epub Apr. 16, 2011.

* cited by examiner

*Primary Examiner* — Umamaheswari Ramachandran
(74) *Attorney, Agent, or Firm* — Wolf, Greenfield & Sacks, P.C.

(57) ABSTRACT

The invention relates to novel veterinary compositions comprising an effective amount of a neonicotinoid compound and an effective amount of a N-arylpyrazole compound. The invention also relates to the use of such compositions for controlling ectoparasites in a non-human mammal.

5 Claims, No Drawings ns: imidacloprid/permethrin and metaflumizone/amitraz (Dryden et al., Veterinary Therapeutics, 2008, 9, 15-25 and Tielemans et al., Parasite, 2010, 17, 343-348).

COMPOSITIONS AND USES THEREOF FOR CONTROLLING ECTOPARASITES IN NON-HUMAN MAMMALS

RELATED APPLICATIONS

This Application is a divisional application of U.S. application Ser. No. 15/747,374, filed Jan. 24, 2018 entitled "COMPOSITIONS AND USES THEREOF FOR CONTROLLING ECTOPARASITES IN NON-HUMAN MAMMALS" which is a national stage filing under 35 U.S.C. § 371 of International Patent Application Serial No. PCT/EP2016/067561, entitled "COMPOSITIONS AND USES THEREOF FOR CONTROLLING ECTOPARASITES IN NON-HUMAN MAMMALS," which has an international filing date of Jul. 22, 2016, which claims foreign priority benefits under 35 U.S.C. § 119(a)-(d) or 35 U.S.C. § 365(b) of European Application No. 15306211.2, filed Jul. 24, 2015, the entire disclosure of each of which is incorporated herein by reference in its entirety.

FIELD OF THE INVENTION

The present invention relates to novel compositions in the field of veterinary medicine, particularly useful for controlling ectoparasites in non-human mammals.

BACKGROUND OF THE INVENTION

Non-human mammals, particularly domestic animals or pets such as dogs or cats, are often susceptible to parasites infestations and may serve as hosts for a large number of ectoparasites. In view of the increasing of domestic animals in the society, the control of parasites and treatment of parasites infestations has been one of the primary objectives of veterinary pharmaceutical companies, not only because of the discomfort of said infestations, but also because of the possible transmission of said infestations to animals and human beings.

In this context, compositions comprising one or several active ingredients as insecticides have been developed for treating parasites infestations and/or controlling parasites. These insecticides are often used according to their effectiveness against the target parasite as well as their costs and, today, they are many chemical compounds that can be used for controlling ectoparasites in animals. Among these chemicals, the organochlorates, organophosphorates, pyrethrins, pyrethroids, arylpyrazoles macrocyclic lactones, neonicotinoids, and insect growth regulators (IGR) may be cited.

Formulations based on N-arylpyrazoles and the associations thereof for controlling ectoparasites in dogs and cats are disclosed in many documents. Particularly, US 2011/0092560 discloses formulations comprising fipronil for controlling fleas, acari and ticks. Combinations of fipronil and an additional insecticide are also disclosed. For instance, BRP19702150 4 discloses formulations comprising fipronil combined with an insect growth inhibitor to control fleas and ticks. WO 2011/038024 discloses spot-on pesticide compositions comprising fipronil, a pyrethroid compound, and optionally an insect growth regulator. The company Merial also studied the efficacy of the of fipronil combined with (S)-methoprene against *Dermacentor variabilis* (American Dog Tick) and *Dermacentor reticulatus* (European Dog Tick) on dogs and compared it to two commercial combinations: imidacloprid/permethrin and metaflumizone/amitraz (Dryden et al., Veterinary Therapeutics, 2008, 9, 15-25 and Tielemans et al., Parasite, 2010, 17, 343-348).

Other documents also disclose formulations based on neonicotinoids combined with an additional insecticide such as pyrethroid compound. For instance, CA 2,564,234 discloses composition containing dinotefuran and a pyrethroid compound for controlling parasitic arthropods on animals. More particularly, WO 2014/060960 discloses the use of the specific combination dinotefuran/flumethrin for the treatment and prevention of fleas and ticks on dogs and cats.

As briefly illustrated above, combinations of insecticides and, more particularly, compositions comprising N-arylpyrazoles or neonicotinoids combined to a pyrethroid have been investigated for the control of ectoparasites but are not always satisfactory. Indeed, an ectoparasite resistance may appear even when high concentrations of a single insecticide are used, thereby limiting their efficacy. Also, high concentrations of insecticides are more expensive and result in a greater likehood that the animal will suffer adverse effects from treatment such as skin discoloration, local hair loss, itching, redness, excessive salivation and neurotoxicity.

Therefore, there is still a need to develop and formulate new compositions comprising one or more insecticides in order to improve the control of ectoparasites in non-human mammals while avoiding adverse effects and resistance development.

SUMMARY OF THE INVENTION

In this context, the inventors surprisingly demonstrated that a combination of a neonicotinoid compound and a N-arylpyrazole compound improved the control of ectoparasites in non-human mammals with a strong synergistic effect.

The present invention therefore relates to a veterinary composition comprising an effective amount of a neonicotinoid compound and an effective amount of a N-arylpyrazole compound.

In a preferred embodiment, the neonicotinoid compound is dinotefuran, derivatives, metabolites or salts thereof. In a further preferred embodiment the N-arylpyrazole compound is fipronil, derivatives, metabolites or salts thereof.

In a particular embodiment, the ratio of the neonicotinoid compound to the N-arylpyrazole compound is from about 6:1 to about 1:6, preferably from about 2:1 to about 1:3, even more preferably about 1:1.5.

Another object of the invention is the use of the veterinary composition as defined herein for the control of ectoparasites in a non-human mammal.

In a preferred embodiment, the ectoparasites are fleas and/or ticks. In a further preferred embodiment, the non-human mammal is a dog or a cat.

In a particular embodiment, the composition used is intended for topical application. More particularly, the composition is a spot-on, a pour-on or a line-on composition.

A further object of the invention is a composition as defined herein, for use in the treatment of ectoparasites infestations in a non-human mammal.

A further object of the invention is a kit comprising (a) one compartment comprising a neonicotinoid compound, preferably dinotefuran, derivatives, metabolites or salts thereof and (b) a second compartment comprising a N-arylpyrazole compound, preferably fipronil, derivatives, metabolites or salts thereof, as a combined preparation for simultaneous, separate or sequential use, in particular for controlling ectoparasites in a non-human mammal.

In a preferred embodiment, the amounts of the neonicotinoid compound in (a) and N-arylpyrazole in (b) are such that the ratio of the neonicotinoid compound to the N-arylpyrazole compound is from about 6:1 to about 1:6, preferably from about 2:1 to about 1:3, more preferably about 1:1.5.

A further object of the invention is a kit as defined herein, further comprising a package leaflet or user instruction including the information that said preparation is to be used for controlling ectoparasites, preferably fleas and/or ticks in a non-human mammal, preferably in a dog or a cat.

DETAILED DESCRIPTION OF THE INVENTION

The inventors have surprisingly demonstrated that compositions comprising a neonicotinoid compound, particularly dinotefuran, and a N-arylpyrazole, particularly fipronil, improved the control of ectoparasites. Particularly, the present invention relates to an antiparasitic veterinary composition comprising synergistic effective amounts of a neonicotinoid compound and a N-arylpyrazole compound.

More particularly, the inventors have shown that a ratio of dinotefuran to fipronil in a range from about 6:1 to about 1:6, preferably about 1:1.5 had a synergistic action against ectoparasites such as fleas and ticks. A synergistic effect is present when the action of the active compound combinations exceeds the total of the actions of the active compounds when applied individually.

Even more particularly, the inventors have surprisingly observed that low amounts of dinotefuran and fipronil combination in such ratio allowed to kill the totality of fleas 48 hours after exposure while maintaining a parasiticide activity against ticks.

Accordingly, the present invention relates to a veterinary composition comprising an effective amount of a neonicotinoid compound and an effective amount of a N-arylpyrazole compound. Particularly, the present invention relates to a veterinary composition comprising an effective amount of a neonicotinoid compound and an effective amount of a N-arylpyrazole compound for controlling ectoparasites in non-human mammals.

As used herein, the expressions "controlling ectoparasites" and "control of ectoparasites" comprise the reduction, the elimination, the killing, the prevention and/or the treatment of ectoparasites in non-human mammals.

The term "ectoparasites" corresponds to a parasite that lives permanently or occasionally on the surface or the skin of a host organism. By way of examples of ectoparasites, arthropod parasites and acari may be cited. Arthropod parasites include without limitation fleas, lice, flies, sand flies and mosquitoes. Acari include without limitation ticks and mites.

Within the context of the invention, the expression "effective amount" means the quantity of the neonicotinoid compound and the N-arylpyrazole compound capable of causing a sufficient control of ectoparasites as above defined. For instance, a sufficient control of ectoparasites is obtained when at least 50%, 60%, preferably 70%, even more preferably at least 80% of the ectoparasites are killed. The evaluation of the percentage (%) corresponds to the number of ectoparasites that are eliminated or killed relative to the total number of ectoparasites. For instance a control of at least 50% means that at least half of the ectoparasites are eliminated or killed and a control of 100% means that the totality of the ectoparasites are eliminated or killed.

The invention also concerns a method for controlling ectoparasites in a non-human mammal comprising administering to said non-human mammal a veterinary composition comprising an effective amount of a neonicotinoid compound, preferably dinotefuran, and an effective amount of a N-arylpyrazole compound, preferably fipronil. In a preferred embodiment, the method controls at least about 50%, about 60%, about 70%, preferably at least about 80% of ectoparasites in said non-human mammal.

The term "about" will be understood by a person of ordinary skill in the art and will vary to some extent on the context in which it is used. If there are uses of the term which are not clear to persons of ordinary skill in the art given the context in which it is used, "about" will mean up to plus or minus 20%, preferably 10% of the particular term.

Neonicotinoid compounds are a class of neuro-active insecticides chemically similar to nicotine. They exhibit an agonist activity for the nicotinic acetylcholine receptors agonists and cause a strong stimulation of nerve cells involving paralysis and death of the parasite with affecting the host animal receptors making them relatively innocuous to the mammals and humans. They have been introduced on market in the 90's and are particularly active against ectoparasites such as fleas, flies and lice. Typical neonicotinoid compounds include without limitation imidacloprid, thiamethoxam, clothianidin, acetamiprid, thiacloprid, dinotefuran, nitenpyram, imidaclothiz, huanyanglin, guadipyr, paichongding, cycloxaprid and the derivatives or salts thereof.

A preferred neonicotinoid compound of the invention is dinotefuran and the derivatives, metabolites or salts thereof. As used in the present description, the term "dinotefuran" can also comprises its derivatives or analogs, metabolites, and salts.

Dinotefuran has been described by the company Mitsui Toatsu Chemicals, Inc. in EP 0 649 845 and has been developed for controlling insect pests. Dinotefuran, also called 2-methyl-l-nitro-3-[(tetrahydro-3-furanyl) methyl] guanidine, has the following formula:

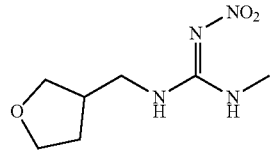

Neonicotinoids and especially dinotefuran are subjected to metabolism in non-human mammals and as a result, metabolites may induce a long-lasting action of neonicotinoids against ectoparasites. The principal metabolic pathways of dinotefuran in mammals involve N-demethylation, nitro reduction, and N-methylene hydroxylation accompanied by amine cleavage. The metabolites of dinotefuran comprise the compounds as disclosed by Simon-Delso et al. (*Systemic insecticides (neonicotinoids and fipronil): trends, uses, mode of action and metabolites*, Environ. Sci. Pollut. Res., 2015, 22:5-34) and by Ford K A and Casida J E (Unique and common metabolites of thiamethoxam, clothianidin, and dinotefuran in mice, Chem. Res. Toxicol., 2006, 19:1549-1556; Neonicotinoid metabolism: compounds, substituents, pathways, enzymes, organisms, and relevance, J. Agric. Food Chem., 2011, 59:2923-2931) and FAO dinotefuran (http://www.fao.org/fileadmin/templates/agphome/documents/PestsPesticides/JMPR/Evaluation12/Dinotefuran.pdf). Typically, the metabolite of dinotefuran comprise, without limitation, N-desmethyl dinotefuran (2-nitro-1-(tetrahydro-3-furylmethyl)guanidine), DIN-NNO, DIN-dm-NNO, DIN-NNH2, 1-methyl-3-(tetrahydro-3-furylmethyl)guanidine, 3-(tetrahydro-3-furylmethyl)guanidine, 1-methyl-3-(tetrahydro-3-furylmethyl)urea, 3-(tetrahydro-3-furylmethyl)urea, 2-hydroxy-dinotefuran, 4-hydrox-dinotefuran, 1,3-diazinane aminocarbinol, DIN-b (derivative of DIN-dm), DIN-e (guanidine derivative of DIN-a), DIN-f (guanidine derivative of DIN-b), DIN-g (derivative of DIN-5-OH), DIN-h (desmethyl-g), DIN-I (nitroso derivative of DIN-g), DIN-j (nitrosoderivative of DIN-h), DIN-k (guanidine derivative of DIN-h), tetrahydrofuran carboxaldehyde (3-furfural), tetrahydrofuran alcohol (3-furfuryl alcohol), tetrahydrofuran-3carboxylic acid, 4-hydroxy-tetrahydrofuran-3-carboxylic acid, tetrahydrofuran-3-yl-methylamine, 1-[4-hydroxy-2-(hydroxymethyl)butyl]-3-methyl-2-nitro guanidine, and 3-hydroxy dinotefuran.

Typically, the derivatives or analogs of dinotefuran comprise all the compounds as disclosed in the EP 0 649 845 patent. More particularly, the derivatives or analogs of dinotefuran comprise, without limitation, 1-[{(tetrahydro-3-furanyl)methyl}amino]-1-methylamino-2-nitroethylene, 1-[{(tetrahydro-3-furanyl)methyl}amino]-1-ethylamino-2-nitroethylene, 1-[{(tetrahydro-3-furanyl)methyl}amino]-1-dimethylamino-2-nitroethylene, 1-[{(tetrahydro-3-furanyl)methyl}amino]-1-(1-pyrrolidinyl)-2-nitroethylene, 1-[N-{(tetrahydro-3-furanyl)methyl}-N-methylamino]-1-methylamino-2-nitroethylene, 1-[N-{(tetrahydro-3-furanyl)methyl}-N-propylamino]-1-methylamino-2-nitroethylene, 1-[N-{(tetrahydro-3-furanyl)methyl}-N-propylamino]-1-ethylamino-2-nitroethylene, 1-{(tetrahydro-3-furanyl)methyl}-2-nitro-3-methylguanidine, N-{(tetrahydro-3-furanyl)-methyl}-N-(methyl)nitroguanidine, 1-{(tetrahydro-3-furanyl)methyl}-1-ethyl-2-nitro-3-methylguanidine, N-(tetrahydro-3-furanyl)-methyl-N'-cyano(methylthio)formamidine, N-cyano-N'-{(tetrahydro-3-furanyl)methyl}acetamidine, N-cyano-N'-{(tetrahydro-3-furanyl)methyl}-N-methylacetamidine, N-[4-{(2-methyl)tetrahydrofuranyl}methyl]-N'-methyl-N"-nitroguanidine, 1-{(tetrahydro-3-furanyl)methyl}-1,2-dicyclohexylcarbonyl-2-methyl-3-nitroguanidine, 1-{(tetrahydro-3-furanyl)methyl}-1,2-diethylcarbonyl-2-methyl-3-nitroguanidine, 1-{(tetrahydro-3-furanyl)methyl}-1,2-dimethoxycarbonyl-2-methyl-3-nitroguanidine, and 1-{(tetrahydro-3-furanyl)methyl}-1,2-dibenzoyl-2-methyl-3-nitroguanidine.

N-arylpyrazole compounds are a class of neuro-active insecticides with efficacy against a broad spectrum of tick species. They achieves their efficacy by disrupting the central nervous system by blocking the passage of chloride ions through the GABA (gamma-amiobutyric acid) receptor and glutamate-gated chloride channels (GluCl), components of the central nervous system. This disruption causes hyperexcitation of contamined nerves and muscles, which results to the death of the tick. Typical N-arylpyrazole compounds include without limitation ethiprole, pyriprole, fipronil, sisapronil, butene fipronil and the derivatives or salts thereof.

A preferred N-arylpyrazole compound of the invention is fipronil and the derivatives or salts thereof. As used herein, the term "fipronil" can also comprise its derivatives or analogs, metabolites, and salts.

Fipronil has been discovered at end of the 80's and has been placed on the market under the patent EP 0 295 117. Fipronil, also called (RS)-5-amino-1-[2,6-dichloro-4-(trifluoromethyl)phenyl]-4-(trifluoromethylsulfinyl)-1H-pyrazole-3-carbonitrile or fluocyanobenpyrazole has the following formula:

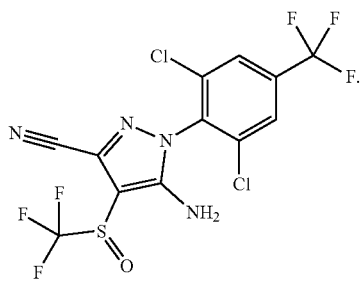 [SMILES: N#Cc1nn(-c2c(Cl)cc(C(F)(F)F)cc2Cl)c(N)c1S(=O)C(F)(F)F]

N-arylpyrazole and especially fipronil are subjected to metabolism in non-human mammals and as a result, metabolites may induce a long-lasting action of N-arylpyrazole against ectoparasites. In mammals, fipronil can be metabolized at its trifluoromethylsulfinyl or cyano moieties through three major pathways: (1) oxidation at the sulfinyl moiety to form fipronilsulfone; (2) reduction at the sulfinyl moiety yielding fipronilsulfide; and (3) by hydrolysis of the cyano moiety to form fipronil-amide followed by further hydrolysis to the corresponding carboxylic acid (5-amino-1-(2,6-dichloro-4-trifluoromethylphenyl)-4-trifluoromethylsulfinyl pyrazole-3-carboxylic acid). The metabolites of fipronil comprise the compounds as disclosed by Simon-Delso et al. (*Systemic insecticides (neonicotinoids and fipronil): trends, uses, mode of action and metabolites*, Environ. Sci. Pollut. Res., 2015, 22:5-34), and in the Draft Assessment Report (DAR) (2005, *Initial risk assessment provided by the rapporteur Member State France for the existing active substance fipronil of the second stage of the review programme referred to in Article 8(2) of Council Directive 91/414/EEC*) and FAO fipronil (http://www.fao.org/fileadmin/templates/agphome/documents/PestsPesticides/JMPR/Evaluation01/08Fipronil.pdf). Typically, the metabolite of fipronil comprise, without limitation, 5-amino-3-cyano-1-(2,6-dichloro-4-trifluoromethylphenyl) pyrazole, 5-amino-1-[2,6-dichloro-4-(trifluoromethyl)phenyl]-4-Rtrifluoromethyl) thiol-1H-pyrazole-3-carbonitrile, 5-amino-1-[2,6-dichloro-4-(trifluoromethyl)phenyl]-4-[(trifluoromethyl) sulfonyl]-1H-pyrazole-3-carbonitrile, 5-amino-1-[2,6-dichloro-4-(trifluoromethyl)phenyl]-4-[1R,S)-(trifluoromethyl)]-1H-pyrazole-3-carbonitrile, 5-amino-3-cyano-1-(2,6-dichloro-4-trifluoromethylphenyl)-pyrazole-4-sulfonic acid, 5-amino-3-carbamyl-1-(2,6-dichloro-4-trifluoromethylphenyl)-4-trifluoromethylsulfonylpyrazole, 5-amino-3-carbamyl-1-(2,6-dichloro-4-trifluoromethylphenyl)-4-trifluoromethylsulfinylpyrazole, 5-amino-3-carbamyl-1-(2,6-dichloro-4-trifluoromethylphenyl)-4-trifluoromethylsulfinylpyrazole-3-carboxylic acid, 5-amino-1-(2,6-dichloro-4-trifluoromethylphenyl)-4-trifluoromethylsulfonylpyrazole-3-carboxylic acid, 1-(2,6-dichloro-4-trifluoromethylphenyl)-3-amino-5-amino-4-trifluoromethylsulfonylpyrazole, 5-amino-3-cyano-1-(2,6-dichloro-4-trifluoromethylphenyl)pyrazole-4-carboxylic acid, 2-[[2,6-dichloro-4-(trifluoromethyl)phenyl]diazenyl]acetonitrile, Ring-opened 5-amino-3-cyano-1-(2,6-dichloro-4-trifluoromethylphenyl)pyrazole-3,4-dicarboxylic acid, and RPA 106681.

Typically, the derivatives or analogs of fipronil comprise all the compounds as disclosed in the EP 0 295 117 patent. More particularly, the derivatives or analogs of fipronil comprise, without limitation, 5-amino-3-cyano-1-(2,6-dichloro-4-trifluoro-methylphenyl)-4-trifluoromethylthiopyrazole, 5-amino-3-cyano-1-(2,6-dichloro-4-trifluoromethoxyphenyl)-4-trifluoromethylthiopyrazole, 5-amino-3-cyano-1-(2,6-dichloro-4-difluoro-methoxyphenyl)-4-trifluoromethylthiopyrazole, 5-amino-1-(2-chloro-4-trifluoromethyl-phenyl)-3-cyano-4-trifluoromethylthiopyrazole, 5-amino-3-cyano-1-(2,4,6-trichlorophenyl)-4-trifluoromethylthiopyrazole, 5-amino-3-cyano-1-(2,6-dibromo-4-trifluoromethylphenyl)-4-trifluoromethylthiopyrazole, 5-amino-1-(2-bromo-4-trifluoromethylphenyl)-3-cyano-4-trifluoromethylthiopyrazole, 5-amino-3-cyano-1-(2,6-dichloro-4-trifluoromethylphenyl)-4-difluoromethylthiopyrazole, 5-amino-3-cyano-1-(2,6-dichloro-4-trifluoromethylphenyl)-4-heptafluoropropylthiopyrazole, 5-amino-1-(2-bromo-6-chloro-4-trifluoromethylphenyl)-3-cyano-4-trifluoromethylthiopyrazole, 5-amino-3-cyano-1-(2,6-dichloro-4-trifluoro-methylphenyl)-4-trichloromethylthiopyrazole, 5-amino-3-chloro-1-(2,6-dichloro-4-trifluoromethylphenyl)-4-trifluoromethylthiopyrazole, 5-amino-3-bromo-1-(2,6-dichloro-4-trifluoromethylphenyl)-4-trifluoromethylthiopyrazole, 5-amino-1-(2,6-dichloro-4-trifluoromethylphenyl)-3-fluoro-4-trifluoromethylthiopyrazole, 5-amino-4-chlorodifluoromethylthio-3-cyanol-(2,6-dichloro-4-trifluoromethylphenyl)pyrazole, 5-chloro-3-cyano-1-(2,6-dichloro-4-trifluoromethylphenyl)-4-trifluoromethylthiopyrazole, 5-amino-3-chloro-1-(2,6-dichloro-4-trifluoromethylphenyl)-4-methanesulphonylpyrazole, 3-cyano-1-(2,6-dichloro-4-trifluoromethylphenyl)-5-ethoxymethyleneamino-4-trifluoromethylthiopyrazole, 3-cyano-1-(2,6-dichloro-4-trifluoromethylphenyl)-5-ethoxyethylideneamino-4-trifluoromethylthiopyrazole, 3-cyano-1-(2,6-dichloro-4-trifluoromethylphenyl)-5-ethoxymethyleneamino-4-methanesulphonylpyrazole, 5-acetamido-3-cyano-1-(2,6-dichloro-4-trifluoro-methylphenyl)-4-trifluoromethylthiopyrazole, 3-cyano-1-(2,6-dichloro-4-trifluoromethylphenyl)-5-bis(propionyl)amino-4-trifluoromethylthiopyrazole, 3-cyano-1-(2,6-dichloro-4-trifluoromethylphenyl)-5-propionamido-4-trifluoromethylthiopyrazole, 5-acetamido-3-cyano-1-(2,6-dichloro-4-trifluoro-methylphenyl)-4-methanesulphonylpyrazole, 3-cyano 1-(2,6-dichloro-4-trifluoromethylphenyl)-4-trifluoromethylthio-5-trimethylacetamidopyrazole, 3-cyano-1-(2,6-dichloro-4-trifluoromethylphenyl)-5-bis (methoxycarbonyl)amino-4-trifluoro-methylthiopyrazole, 3-cyano-1-(2,6-dichloro-4-trifluoromethylphenyl)-5-bis(ethoxycarbonyl)amino-4-trifluoromethylthiopyrazole, 5-chloroacetamido-3-cyano-1-(2,6-dichloro4-trifluoromethylphenyl-4-trifluoromethylthiopyrazole, 3-cyano-1-(2,6-dichloro-4-trifluoromethylphenyl)-5-bis (ethoxyc arbonyl)amino-4-methanesul-phonylpyrazole, 3-cyano-1-(2,6-dichloro-4-trifluoromethylphenyl)-4-methanesulphonyl-5-trimethylacetamidopyrazole, 3-cyano-1-(2,6-dichloro-4-trifluoromethylphenyl)-5-dimethylamino-4-trifluoromethylthiopyrazole, 3-cyano-1-(2,6-dichloro-4-trifluoromethylphenyl)-5-isopropylamino-4-trifluoromethylthiopyrazole, 3-cyano-1-(2,6-dichloro-4-trifluoromethylphenyl)-5-propylamino-4-trifluoromethylthiopyrazole, 3-cyano-1-(2,6-dichloro-4-trifluoromethyl-phenyl)-5-dipropylamino-4-trifluoromethylthiopyrazole, 3-cyano-1-(2,6-dichloro-4-trifluoromethylphenyl)-5-bis(propargyl)amino-4-trifluoromethylthiopyrazole, 3-cyano-1-(2,6-dichloro-4-trifluoromethylphenyl)-5-methylamino-4-methanesulphonylpyrazole, 5-bromo-3-cyano-1-(2,6-dichloro-4-trifluoroethylphenyl)-4-trifluoromethanesulphonylpyrazole, 5-bromo-3-cyano-1-(2,6-dichloro-4-trifluoro-methylphenyl)-4-trifluoromethylthiopyrazole, 5-bromo-3-cyano-1-(2,6-dichloro-4-trifluoromethylphenyl)-4-methanesulphonylpyrazole, 5-amino-3-bromo-1-(2,6-dichloro-4-trifluoromethylphenyl)-4-methanesulphonylpyrazole, 3-bromo-1-(2,6-dichloro-4-trifluoromethylphenyl)-4-methanesulphonylpyrazole, 3-cyano-1-(2,6-dichloro-4-trifluoromethylphenyl)-4-trifluoromethylthiopyrazole, 3-cyano-1-(2,6-dichloro-4-trifluoromethylphenyl)-4-trifluoromethanesulphonylpyrazole, 3-cyano-1-(2,6-dichloro-4-trifluoromethoxyphenyl)-4-trifluoromethylthiopyrazole, 3-cyano-1-(2,6-dichloro-4-trifluoromethylphenyl)-4-methanesulphonylpyrazole, 3-cyano-1-(2,6-dichloro-4-trifluoromethylphenyl)-5-iodo-4-trifluoromethylthiopyrazole, 3-cyano-1-(2,6-dichloro-4-trifluoromethylphenyl)-5-iodo-4-trifluoromethanesulphonylpyrazole, 5-amino-1-(2,6-dichloro-4-trifluoromethylphenyl)-3-iodo-4-methanesulphonylpyrazole, 1-(2,6-dichloro-4-trifluoromethylphenyl)-3-iodo-4-methanesulphonylpyrazole, 1-(2,6-dichloro-4-trifluoromethylphenyl)-3-iodo-4-trifluoromethylthiopyrazole, 5-amino-3-cyano-1-(2,6-dichloro-4-trifluoromethylphenyl)-4-trifluoromethanesulphonylpyrazole, 5-amino-3-cyano-1-(2,6-dichloro-4-trifluoromethylphenyl)-4-trifluoromethylsulphinylpyrazole, 5-amino-3-cyano-1-(2,6-dichloro-4-trifluoro-methoxyphenyl)-4-trifluoromethanesulphonylpyrazole, 5-amino-3-cyano-1-(2,6-dichloro-4-trifluoromethoxyphenyl)-4-trifluoromethylsulphinylpyrazole, 3-cyano-1-(2,6-dichloro-4-trifluoromethylphenyl)-4-trifluoromethylsulphinylpyrazole, 5-amino-3-cyano-1-(2,6-dichloro-4-trifluoromethylphenyl)-4(1-methylprop-2-ynylsulphinyl)pyrazole, 5-amino-3-cyano-1-(2,6-dichloro-4-trifluoromethylphenyl)-4-methylsulphinylpyrazole, 5-amino-3-cyano-1-(2,6-dichloro-4-trifluoromethylphenyl)-4-isopropylsulphinylpyrazole, 5-amino-3-bromo-1-(2,6-dichloro-4-trifluoro-methylphenyl)-4-trifluoromethylsulphinylpyrazole, 5-amino-4-tert-butanesulphonyl-3-cyano-1-(2,6-dichloro-4-trifluoromethylphenyl)pyrazole, 3-cyano-1-(2,6-dichloro-4-trifluoromethylphenyl)-5-propylamino-4-trifluoromethylsulphonylpyrazole, 5-acetamido-3-cyano-1-(2,6-dichloro-4-trifluoromethylphenyl)-4-trifluoromethanesulphonylpyrazole, 1-(2,6-dichloro-4-trifluoromethylphenyl)-4-methanesulphonyl-3-nitropyrazole, 5-amino-1-(2,6-dichloro-4-trifluoromethylphenyl)-4-methanesulphonyl-3-nitropyrazole, 1-(2,6-dichloro-4-trifluoromethylphenyl)-3-nitro-4-trifluoromethylsulphinylpyrazole, 5-amino-1-(2-bromo-6-chloro-4-trifluoromethyl-phenyl)-3-cyano-4-methanesulphonylpyrazole, 5-amino-1-(2,6-dichloro-4-trifluoromethoxyphenyl)-3-cyano-4-methanesulphonylpyrazole, 3-acetyl-5-amino-1-(2,6-dichloro-4-trifluoromethylphenyl)-4-methanesulphonylpyrazole, 5-amino-3-cyano-1-(2,6-dichloro-4-trifluoromethylphenyl)-4-methylthiopyrazole, 5-amino-3-cyano-1-(2,6-dichloro-4-trifluoromethylphenyl)-4-ethylthiopyrazole, 5-amino-3-cyano-1-(2,6-dichloro-4-trifluoromethylphenyl)-4-propylthiopyrazole, 5-amino-3-cyano-1-(2,6-dichloro-4-trifluoromethylphenyl)-4- isopropylthiopyrazole, 5-amino-3-cyano-1-(2,6-dichloro-4-trifluoromethylphenyl)-4-(2-methylpropylthio)pyrazole, 5-amino-3-cyano-1-(2,6-dichloro-4-trifluoromethylphenyl)-4-(1-methylpropylthio)pyrazole, 4-allylthio-5-amino-3-cyano-1-(2,6-dichloro-4-trifluoromethylphenyl)pyrazole, 5-amino-3-cyano-1-(2,6-dichloro-4-trifluoromethylphenyl)-4-(prop-2-ynylthio)pyrazole, 5-amino-3-cyano-1-(2,6-dichloro-4-trifluoromethylphenyl)-4-(1-methylprop-2-ynyl-thio)pyrazole, 5-amino-3-bromo-1-(2,6-dichloro-4-trifluoromethylphenyl)-4-methylthiopyrazole, 5-amino-3-cyano-1-(2,6-dichloro-4-trifluoromethylphenyl)-4-tert-butylthiopyrazole, 5-amino-3-bromo-1-(2,6-dichloro-4-trifluoromethylphenyl)-4-methylsulphinylpyrazole, 5-amino-3-cyano-1-(2,6-dichloro-4-trifluoromethylphenyl)-4-ethanesulphonylpyrazole, 3-cyano-1-(2,6-dichloro-4-trifluoromethylphenyl)-5-methylamino-4-trifluoromethylthiopyrazole, 3-cyano-1-(2,6-dichloro-4-trifluoromethylphenyl)-5-(N-ethoxycarbonyl-N-methyl)amino-4-trifluoromethylthiopyrazole, 3-cyano-1-(2,6-dichloro-4-trifluoromethylphenyl)-5-trifluoroacetamido-4-trifluoromethylthiopyrazole, 3-cyano-1-(2,6-dichloro-4-trifluoromethylphenyl)-5-(ethoxycarbonylamino)-4-trifluoromethylthiopyrazole, 3-acetyl-1-(2,6-dichloro-4-trifluoromethylphenyl)-4-trifluoromethylthiopyrazole, 1-(2,6-dichloro-4-trifluoromethylphenyl)-3-formyl-4-trifluoromethylthiopyrazole, 5-amino-1-(2,6-dichloro-4-trifluoromethylphenyl)-3-formyl-4-trifluoromethylthiopyrazole, 3-cyano-1-(2,6-dichloro-4-trifluoromethyl-phenyl)-5-fluoro-4-trifluoromethanesulphonylpyrazole, 5-amino-3-cyano-4-dichlorofluoromethylthio-1-(2,6-dichloro-4-trifluoromethylphenyl)pyrazole, 5-amino-3-chloro-1-(2,6-dichloro-4-trifluoromethylphenyl)-4-trifluoromethanesulphonylpyrazole, 5-amino-3-cyano-1-(2,6-dichloro-4-trifluoromethylphenyl)-4-pentafluoroethylthiopyrazole, 3-cyano-1-(2,6-dichloro-4-trifluoromethylphenyl)-5-dimethylamino-4-trifluoromethylsulphinylpyrazole, 3-cyano-1-(2,6-dichloro-4-trifluoromethylphenyl)-5-iodo-4-trifluoromethylsulphinylpyrazole, 5-bromo-3-cyano-1-(2,6-dichloro-4-trifluoromethylphenyl)-4-trifluoromethylsulphinylpyrazole, 5-acetamido-3-cyano-1-(2,6-dichloro-4-trifluoromethylphenyl)-4-trifluoromethylsulphinylpyrazole, 3-cyano-1-(2,6-dichloro-4-trifluoromethylphenyl)-5-bis(ethoxycarbonyl)amino-4-trifluoromethanesulphonylpyrazole, 3-cyano-1-(2,6-dichloro-4-trifluoromethylphenyl)-5-ethoxycarbonylamino-4-trifluoromethane-sulphonylpyrazole, 3-cyano-1-(2,6-dichloro-4-trifluoromethylphenyl)-5-ethoxymethyleneamino-4-trifluoromethanesulphonylpyrazole, 5-amino-4-(2-chloro-1,1,2-trifluoroethylthio)-3-cyano-1-(2,6-dichloro-4-trifluoromethylphenyl)pyrazole, and 3-cyano-1-(2,6-dichloro-4-trifluoromethylphenyl)-5-dimethylamino-4-trifluoromethanesulphonylpyrazole.

Within the context of the invention, the salts of dinotefuran and fipronil correspond to its acceptable pharmaceutically salts. An acceptable pharmaceutically salt includes inorganic as well as organic acids salts. Representative examples of suitable inorganic acids include hydrochloric, hydrobromic, hydroiodic, phosphoric and the like. Representative examples of suitable organic acids include formic, acetic, trichloroacetic, propionic, benzoic, cinnamic, fumaric, maleic, methanesulfonic and the like.

Within the context of the present invention, the amounts of the active compounds or ingredients are preferably expressed by parts per million (ppm). Said active compounds can be diluted in water with a density of 1 kg/L. Therefore, one ppm corresponds to 1 mg/kg or 1 mg/L. In the present invention, the concentrations of the active compounds are expressed in ppm (equivalent to mg/L). Consequently, the ratio of such ingredients is also a concentration ratio.

In a particular embodiment, the compositions of the invention comprise a concentration ratio of the neonicotinoid compound to the N-arylpyrazole compound from about 6:1 to about 1:6, preferably from about 2:1 to about 1:3, even more preferably about 1:1.5.

Particularly, a synergistic action or effect with the neonicotinoid compound and the N-arylpyrazole compound is obtained with low concentrations, typically in a range from about 1 ppm to about 500 ppm, preferably from about 1 ppm to about 200 ppm, more preferably from about 1 ppm to about 100 ppm, even more preferably from about 1 ppm to about 20 ppm.

In a preferred embodiment, the concentration of the neonicotinoid compound in the compositions of the invention is from about 1 ppm to about 10 ppm.

In a further preferred embodiment, the concentration of the N-arylpyrazole compound is from about 1 ppm to about 15 ppm.

Another object of the invention is the use of a veterinary composition as herein defined for controlling ectoparasites in a non-human mammal.

Ectoparasites are such as defined above and are preferably fleas and/or ticks.

As used herein, non-human mammals include any mammals with the exception of humans being. Preferably, non-human mammals are domestic animals including without limitation companion animals or pets such as dogs, cats, rabbits, ferrets and hamsters. In a more preferred embodiment of the invention, non-human mammals are dogs and cats.

Ectoparasite infestations such as fleas and ticks infestations commonly occur in non-human mammals and household environments and are frequent in tropical and temperate countries.

Fleas are intermediate hosts of the cestode of cats and dogs and cause a large number of infestations such as the dog parasitical filarial (*Dipylidium caninum*), the vector of feline rickettsiosis (*Dipetalonema reconditum*), the cat scratch disease (*Bartonella henseale*), the canine mycoplasmosis (*Mycoplasma haemocanis*) and the feline mycoplasmosis (*Mycoplasma haemofelis*). However, the primary species of flea that infests dogs and cats is *Ctenocephalides felis*. Fleas have also been recently described as being involved in the transmission of feline leukemia and their possible participation in the epidemiology of canine leishmaniosis. Fleas are further implicated in Flea Allergy Dermatitis (FAD) in dogs and cats, which is caused by the action of saliva containing allergenic substances that cause intense skin reactions in hypertensive animals. Typical symptoms include erythema (redness), papules (bumps), pustules (pus-filled bumps), crusts (scabs), hair loss and eczematous skin rash. These symptoms will occur often in upper tail, neck, and down the back of the legs. There is no gender or age predisposition, but most cases occur in animals between two and five years of age.

Tick infestation (or ixodidiosis) is caused mainly by *Rhipicephalus sanguineus* species, which has taken advantage of the growth of large cities and the spread of central heating installed in buildings to disseminate in urban zones, where said species frequently give rise to enormous populations that are difficult to treat and control, causing disease to animals due to blood spoliation, which may cause rashes, itching, loss of appetite, anemia, and in severe cases, the death of the animal. Ticks can transmit innumerable diseases to dogs, such as canine babesiosis (*Babesia canis*) and canine ehrlichiosis (*Ehrlichia canis*).

Another object of the invention is therefore a composition as herein defined for use in a treatment of ectoparasites infestations in a non-human mammal.

A further objet of the invention is a method for controlling ectoparasites and/or treating ectoparasites infestations in a non-human mammal comprising administering to said non-human mammal a veterinary composition comprising an effective amount of a neonicotinoid compound, preferably dinotefuran, and an effective amount of a N-arylpyrazole compound, preferably fipronil.

A further object of the invention is a use of a veterinary composition as herein defined for the manufacture of a medicament for treating ectoparasites infestations in a non-human mammal.

As used herein, the term "treatment" includes, particularly, the preventive treatment of non-human mammals against an infestation or infection. The preventive treatment of a non-human mammal against a disease designates a treatment made before the non-human mammal has been exposed to or in contact with the causative agent of the infestation (e.g., the ectoparasite), or after said exposure/contact but before development of the symptoms or at an early stage of development of the disease.

In a particular embodiment, the term treatment designates the protection of a non-human mammal against an infestation or infection, e.g., against the effect of an exposure to the causative agent, specifically ectoparasites, or against the development of the disease in exposed-non-human mammals. The invention is particularly suited to protect non-human mammals against an infestation or infection disease such as ectoparasite infestation.

The term treatment also includes the alleviation of the symptoms, as well as a delay, reduction or cure of an existing ectoparasite infestation or infection.

The veterinary composition according to the present invention can be in any appropriate forms to suit the requested administration modes, for instance topical, enteral, parenteral, or dermal application. According to the administration mode, the composition of the invention can be a spot-on, a pour-on, a line-on, a spray, a dip, an oral or an injectable composition.

In a preferred embodiment, the composition is in a form intended for topical application. In a more preferred embodiment, the composition of the invention is a pour-on, spot-on or a line-on composition.

The "spot-on" (or "drop spot") composition refers to a composition of topical use that is applied to only one spot of the body of the animal where the animal cannot lick the application area and is preferably localized between the animal's shoulders or neck. From this spot, the active ingredients (neonicotinoid compound and N-arylpyrazole compound) spreads rapidly over the entire body surface, thereby providing generalized protection. The active ingredients translocate through the epidermis, accumulates in sebaceous glands, and is gradually released by the follicular ducts.

The "pour-on" or "line-on" composition refer to a composition of topical use that is continuously applied. The "pour-on" compositions are more particularly applied in big non-human mammals such as horses and cattle, and the "line-on" compositions are more particularly applied in small non-human mammals such as domestic animals as defined above, preferably dogs and cats. Particularly, the "pour-on" and "line-on" compositions are applied from the tail, along the backbone to the shoulders of the animal. More particularly, such compositions are applied against the grain of the animal.

The veterinary compositions of the invention are solid, such as powders, gel or liquid forms and are more preferably a liquid form comprising pharmaceutically acceptable vehicles, such as excipients conventionally used in pharmacy for the preparation of liquid formulations for topical or dermatological administration.

Thus, the compositions of the invention may include, according to the type of formulation, solvents and antioxidants.

Within the context of the invention, the solvent is defined for its availability to homogenously dissolve at least the neonicotinoid compound and the N arylpyrazole compound. A skilled person in the art can appreciate a wide variety of solvents than can be incorporated into the compositions of the invention. However, the solvent should cause minimal cutaneous irritation when applied to the skin of the non-human mammal. Suitable solvents include without limitation xylenes, chlorobenzene, methylene, chloride, chloroform trichloroethane, ethylene chloride benzaldehyde, sulfolane, methyl tert-butyl, propylene diethylcarbonate, ethylene carbonate, alcohols such as methanol, ethanol, propanol, butanol, isopropanol, hexafluoroisopropanol, ketones such as acetone, 2-butanone, 3-methyl-2-butanone, cyclohexanone, amines and amides such as dimethylformamide (DMF), dimethylacetamide (DMAC), N-methyl-2-pyrrolidone (NMP), N-octyl-2-pyrrolidone (NOP), triethylamine, organosulfur such as dimethylsulfoxide (DMSO), nitriles such as acetonitrilacetonitrile, esters such as ethyl acetate, propyl acetate, or amyl acetate, nitrogen heterocycles, such as pyridine, carboxylic acids such as formic acid and acetic acid, ether such as propylene alkyl ether, ethylene alkyl ether, dibutyl alkyl ether, polyglycol ether aryl alkyl or polyglycol, polypropylene glycol or polyethylene glycol units, primary and secondary amines. Preferably, the compositions of the invention comprise DMSO and NMP as solvents. More preferably, the compositions of the invention comprise at least 35% of DMSO by weight, relative to the total weight of the composition. In a particular embodiment, the compositions of the invention do not comprise water or apolar solvent.

An antioxidant can generally be defined as a compound capable of slowing or preventing the oxidation of other molecules such as active ingredients. They act as stabilizers and prevent the various components of the composition from degrading by oxidation processes. They also should not cause irritation to the skin of the non-human mammal when applied to the skin. As antioxidants, butylhydroxyanisol (BHA), butylhydroxytoluene (BHT), ascorbic acid, ascorbyl palmitate, monothioglycerol, propylgallate, sulphur dioxide, tocopherol, and tocopherol acetate may be cited without limitation. Preferably, the compositions of the invention comprise BHA and BHT as antioxidants.

The compositions of the invention may comprise any further excipients currently used in parasiticide compositions such as, without limitation, binders, fillers, disintegrants, preservatives, crystallization inhibitors, diluents, lubricants, pH modifiers, stabilizers and the like.

The term "crystallization inhibitor" means an agent or a substance that inhibits the formation of crystals of the active neonicotinoid and N-arylpyrazole in the solvent, even if the solvents used in the invention fundamentally prevent the crystallization of the asset. These inhibitors include, for example, without limitation, polyvinylpyrrolidone, alcohols polyvinyl copolymers, vinyl acetate and vinyl pyrrolidone, mannitol, glycerol, sorbitol, lecithin, odium carboxymethylcellulose, the derivatives acrylics such as methacrylates and others alike, surfactants anionic such as alkaline stearates, in particular sodium, potassium or ammonium stearate, calcium stearate, triethanolamine stearate; sodium abietate and alkyl sulphates. Such crystallization inhibitors have therefore opposite properties compared to crystallization agents, which promote the formation of crystals. In a particular embodiment, the compositions of the invention do not comprise crystallization agent.

Preferred compositions of the invention comprise:
about 1 to 20%, preferably about 5 to 15%, more preferably about 10% by weight of dinotefuran,
about 1 to 30%, preferably about 5 to 25%, more preferably about 15% by weight of fipronil,
about 35 to 85%, preferably, about 50 to 70%, more preferably about 60% by weight of DMSO, and
about 1 to 30%, preferably about 5 to 25%, more preferably about 15% by weight of NMP,
relative to the total weight of the composition.

The compositions according to the present invention may further comprise at least one pesticide agent in addition to the combination of the neonicotinoid compound and the N-arylpyrazole compound. Said further pesticide agent may be for instance, without limitation, a "growth regulator" (also called "IGR" or "Insect Growth Regulator") such as S-methoprene or methoprene, pyriproxyfen, a chitin inhibitor such as lufenuron, chlorfluazuron, hexaflumuron, cyromazine, and 1-(2,6-difluorobenzoyl)-3-[2-fluoro-4-(1,1,2,3,3,3-hexafluoropropoxy) phenyl urea]; a macrocyclic lactone such as avermectin, typically ivermectin, abamectin, doramectin, eprinomectin, selamectin, and milbemycins such as, milbemycin oxime, moxidectin and abamectin; an organochlorine or organophosphorus compounds such as diazinon, coumaphos, dichlorvos, fenitrothion, fenthion, bendiocarb, tetrachlorvinphos, and chlorpyrifos; a carbamate compounds such as propoxur, carbaryl, metoxadiazone and Fenobucarb; a pyrethroid compounds such as permethrin, deltamethrin, cypermethrin, phenothrin, allethrin, pyrethrin, cyphenothrin, cyfluthrin, fenvalerate, fenpropathrin and transfluthrin; a semicarbazone compound such as metaflumizone; a formamidine compound such as amitraz; an anthelmintic compound such as pyrantel, praziquantel, benzimidazole and imidazothiazole; synergists compounds such as piperonyl butoxide (PBO), octachlorodipropyl ether (S-421), N-(2-ethylhexyl)-bicyclo-[2.2.1]-hept-5-ene-2,3-dicarboximide, isobornyl thiocyanatoacetate (IBTA) and N-(2-ethylhexyl)-1-isopropyl-4-methylbicyclo [2.2.2] oct-5-ene-2,3-dicarboximide.

Another object of the present invention is a kit comprising (a) one compartment comprising a neonicotinoid compound, preferably dinotefuran and the derivatives or salts thereof and (b) a second compartment comprising a N-arylpyrazole compound, preferably fipronil and the derivatives or salts thereof, as a combined preparation for simultaneous, separate or sequential use, in particular for controlling ectoparasites in a non-human mammal.

In a particular embodiment, the amounts of the neonicotinoid compound in (a) and N-arylpyrazole in (b) are such that the ratio of the neonicotinoid compound to the N-arylpyrazole compound is from about 6:1 to about 1:6, preferably from about 2:1 to about 1:3, more preferably about 1:1.5, preferably when both are combined and preferably applied onto the skin.

As used herein, the term "simultaneous" includes that the neonicotinoid compound and the N-arylpyrazole compound are co-administered in a same composition. In this context, both compounds are in intimate contact. The term "simultaneous" also includes that the neonicotinoid compound and the N-arylpyrazole compound are co-administered, i.e. simultaneously.

As used herein, the terms "separate" or "sequential" mean that the neonicotinoid compound and the N-arylpyrazole compound are administered successively. For instance the neonicotinoid compound or the composition comprising the neonicotinoid compound is firstly administered in a non-human mammal and the N-arylpyrazole compound or the composition comprising the N-arylpyrazole compound is secondly administered in the same non-human mammal. In this context, the neonicotinoid compound and the N-arylpyrazole compound are physically sufficiently distinct from being separately or sequentially administrable.

A further object of the invention is a kit as defined above, further comprising a package leaflet or user instruction including the information that said preparation is to be used for controlling ectoparasites, preferably fleas and/or ticks in a non-human mammal, preferably in a dog or a cat.

Further aspects and advantages of the invention will be disclosed in the following experimental section.

EXAMPLES

Example 1

Composition of the Invention

| Ingredients | Weight (g) |
| --- | --- |
| Dinotefuran | 10 |
| Fipronil | 15 |
| DMSO | 60 |
| NMP | 15 |

Example 2

Activity Against Fleas

Material and Methods

Insecticidal activity of dinotefuran, fipronil and dinotefuran/fipronil combinations at different ratios was evaluated using an in vitro coated-vial bioassay. Serial dilutions of test compounds, individually or in combination, were conducted with an acetone/triton solution +0.5% DMSO from a dinotefuran starting dose at 100 ppm and from a fipronil starting dose at 50 ppm. Vials were treated with dinotefuran, fipronil, dinotefuran/fipronil (tested at 6 ratios). Vials were capped and allowed to dry for at least 4 hours before the addition of 10 newly emerged (0-7 days old) unfed adult fleas (*Ctenocephalides felis*). Flea susceptibility was assessed at 6, 24 and 48 hours post-exposure by evaluating mortality. The $EC_{50}$ and $EC_{90}$ values were calculated based on Median-Effect Principle (Chu, 2006. Theoretical Basis, Experimental design, and Computerized Simulation of Synergism and Antagonism in drug Combination studies. *Pharmacological reviews*, 58(3):621-681) using COMPUSYN (version 1.0). EC50 and $EC_{90}$ are defined as the amount of drugs, which causes respectively a 50% and 90% flea mortality. Combination indexes (CI) at $EC_{50}$ and $EC_{90}$ were calculated to characterize the interaction of each combination: synergism (CI<1), antagonism (CI>1) and additive effect (CI=1) and a combination index (CI) values were calculated at 48 hours of exposure to assess the potential for synergistic activity (Chou, Pharmacol. Rev. 2006, 58, 621-681; Chou, *Drug combination studies and their synergy quantification using the Chou-Talalay method*, Cancer. Res., 2010, 70: 440-446).

Results

The results are represented in the following table 1 (Mortality (%) is given at ±10%), table 2 ($EC_{50}$) and table 3 ($EC_{90}$).

TABLE 1

| Ratio (D:F) | Concentration (ppm) | | Mortality (%) | | |
|---|---|---|---|---|---|
| | Dinetofuran (D) | Fipronil (F) | 6 H | 24 H | 48 H |
| 1:0 | 0.412 | 0.000 | 0 | 10 | 0 |
| | 1.235 | 0.000 | 0 | 10 | 20 |
| | 3.704 | 0.000 | 0 | 20 | 50 |
| | 11.111 | 0.000 | 10 | 30 | 60 |
| | 33.333 | 0.000 | 0 | 10 | 80 |
| | 100.000 | 0.000 | 40 | 80 | 90 |
| 6:1 | 0.309 | 0.051 | 0 | 0 | 0 |
| | 0.926 | 0.154 | 0 | 0 | 0 |
| | 2.778 | 0.463 | 0 | 60 | 60 |
| | 8.333 | 1.389 | 0 | 60 | 90 |
| | 25.000 | 4.167 | 10 | 70 | 100 |
| | 75.000 | 12.500 | 20 | 100 | 100 |
| 2:1 | 0.206 | 0.103 | 0 | 0 | 0 |
| | 0.617 | 0.309 | 10 | 10 | 10 |
| | 1.852 | 0.926 | 20 | 20 | 60 |
| | 5.556 | 2.778 | 30 | 30 | 70 |
| | 16.667 | 8.333 | 90 | 90 | 100 |
| | 50.000 | 25.000 | 100 | 100 | 100 |
| 1:1.5 | 0.103 | 0.154 | 0 | 0 | 0 |
| | 0.309 | 0.463 | 0 | 0 | 0 |
| | 0.926 | 1.389 | 10 | 0 | 10 |
| | 2.778 | 4.167 | 30 | 70 | 100 |
| | 8.333 | 12.500 | 20 | 100 | 100 |
| | 25.000 | 37.500 | 40 | 100 | 100 |
| 0:1 | 0.000 | 0.206 | 0 | 0 | 0 |
| | 0.000 | 0.617 | 0 | 0 | 0 |
| | 0.000 | 1.852 | 0 | 0 | 0 |
| | 0.000 | 5.556 | 0 | 0 | 0 |
| | 0.000 | 16.667 | 0 | 0 | 90 |
| | 0.000 | 50.000 | 0 | 80 | 100 |

TABLE 2

| Drug or Drug Combinations (D:F) | Combination Index (CI) | $EC_{50}$ (ppm) | | |
|---|---|---|---|---|
| | | Dinotefuran | Fipronil | Total amount of actives (ppm) |
| D:F = 1:0 | — | 8.05 | — | 8.05 |
| D:F = 0:1 | — | — | 13.83 | 13.83 |
| D:F = 6:1 | 0.36 | 2.69 | 0.45 | 3.14 |
| D:F = 2:1 | 0.34 | 2.10 | 1.05 | 3.15 |
| D:F = 1:1.5 | 0.28 | 1.20 | 1.80 | 3.00 |
| D:F = 1:1 | 0.3 | 1.51 | 1.57 | 3.08 |
| D:F = 1:3 | 0.22 | 0.66 | 1.92 | 2.58 |
| D:F = 1:6 | 0.19 | 0.36 | 2.02 | 2.38 |

TABLE 3

| Drug or Drug Combinations | Combination Index (CI) | $EC_{90}$ (ppm) | | |
|---|---|---|---|---|
| | | Dinotefuran | Fipronil | Total amount of actives (ppm) |
| D:F = 1:0 | — | 50.87 | — | 50.87 |
| D:F = 0:1 | — | — | 73.30 | 73.30 |
| D:F = 6:1 | 0.20 | 9.34 | 1.55 | 10.89 |
| D:F = 2:1 | 0.19 | 7.53 | 3.76 | 11.29 |
| D:F = 1:1.5 | 0.15 | 3.97 | 5.96 | 9.93 |

The results show that:
dinotefuran (ratio D:F=1:0; EC50=8.05 ppm) is more potent than fipronil (ratio D:F=0:1; EC50=13.83) against fleas;
the combinations of the two active ingredients are more potent than any individual active, thereby demonstrating a strong synergy between dinotefuran and fipronil (CI<1 for each ratio) ; and
the best combination is obtained with a ratio D:F=1:1.5.

Example 3

Activity Against Ticks

Material and Methods

Insecticidal activity of dinotefuran, fipronil and dinotefuran/fipronil combinations at different ratios was evaluated using an in vitro coated-vial bioassay. Serial dilutions of test compounds, individually or in combination, were conducted with an acetone/triton solution +0.5% DMSO from a dinotefuran starting dose at 100 ppm and from a fipronil starting dose at 50 ppm. Vials were treated with dinotefuran, fipronil, dinotefuran/fipronil (tested at 6 ratios). Vials were capped and allowed to dry for at least 4 hours before the addition of 10 adult ticks (Rhipicephalus sanguineus). Tick susceptibility was assessed at 12, 24 and 48 hours post-exposure by evaluating mortality.

Results

The results are represented in the following table 4 (Mortality (%) is given at ±10%) and table 5 (EC50).

TABLE 4

| Ratio (D:F) | Concentration (ppm) | | Mortality (%) | | |
|---|---|---|---|---|---|
| | Dinetofuran (D) | Fipronil (F) | 12 H | 24 H | 48 H |
| 1:0 | 0.412 | 0.000 | 0 | 0 | 0 |
| | 1.235 | 0.000 | 0 | 0 | 0 |
| | 3.704 | 0.000 | 0 | 0 | 0 |
| | 11.111 | 0.000 | 0 | 0 | 0 |
| | 33.333 | 0.000 | 0 | 0 | 0 |
| | 100.000 | 0.000 | 0 | 0 | 0 |
| 6:1 | 0.309 | 0.051 | 0 | 0 | 0 |
| | 0.926 | 0.154 | 0 | 0 | 0 |
| | 2.778 | 0.463 | 0 | 0 | 0 |
| | 8.333 | 1.389 | 0 | 0 | 20 |
| | 25.000 | 4.167 | 0 | 10 | 40 |
| | 75.000 | 12.500 | 0 | 50 | 80 |
| 2:1 | 0.206 | 0.103 | 0 | 0 | 0 |
| | 0.617 | 0.309 | 0 | 0 | 0 |
| | 1.852 | 0.926 | 0 | 0 | 20 |
| | 5.556 | 2.778 | 0 | 0 | 30 |
| | 16.667 | 8.333 | 10 | 0 | 30 |
| | 50.000 | 25.000 | 0 | 80 | 90 |
| 1:1.5 | 0.103 | 0.154 | 0 | 0 | 0 |
| | 0.309 | 0.463 | 0 | 0 | 10 |

TABLE 4-continued

| Ratio (D:F) | Concentration (ppm) Dinetofuran (D) | Fipronil (F) | Mortality (%) 12 H | 24 H | 48 H |
|---|---|---|---|---|---|
| | 0.926 | 1.389 | 0 | 0 | 20 |
| | 2.778 | 4.167 | 0 | 10 | 60 |
| | 8.333 | 12.500 | 20 | 80 | 80 |
| | 25.000 | 37.500 | 20 | 70 | 90 |
| 0:1 | 0.000 | 0.206 | 0 | 0 | 0 |
| | 0.000 | 0.617 | 0 | 0 | 10 |
| | 0.000 | 1.852 | 0 | 0 | 0 |
| | 0.000 | 5.556 | 0 | 20 | 60 |
| | 0.000 | 16.667 | 60 | 80 | 100 |
| | 0.000 | 50.000 | 60 | 100 | 100 |

TABLE 5

| Drug or Drug Combinations | $EC_{50}$ (ppm) Dinotefuran | Fipronil | Total amount of actives (ppm) |
|---|---|---|---|
| D:F = 1:0 | >100 | — | 100 |
| D:F = 0:1 | — | 3.77 | 3.77 |
| D:F = 6:1 | >100 | 41.08 | NA |
| D:F = 2:1 | >100 | 19.73 | NA |
| D:F = 1:1.5 | >100 | 7.14 | NA |

The results show that:
dinotefuran (ratio D:F=1:0) is not active against ticks contrary to fipronil;
the acaricidal activity of combinations of the two active ingredients is similar to fipronil alone, thereby demonstrating no negative interaction between both active ingredients; and
the best acaricidal effect is obtained with a ratio D:F=1:1.5.

In conclusion, the inventors have surprisingly demonstrated that a composition comprising a neonicotinoid compound, particularly dinotefuran, and a N-arylpyrazole compound, particularly fipronil, was more potent against ectoparasite than each individual compound, thereby demonstrating a synergistic effect. Particularly, the inventors have demonstrated that such composition comprising low concentrations of dinotefuran and fipronil in a ratio D:F from about 6:1 to about 1:6, preferably about 1:1.5 improved the control of fleas with a synergistic effect while maintaining a control against ticks.

The invention claimed is:

1. A method for controlling fleas in a non-human mammal comprising, administering to the non-human mammal a veterinary composition consisting essentially of an effective amount of dinotefuran or salts thereof and an effective amount of fipronil or salts thereof, wherein the ratio of dinotefuran or salts thereof to fipronil or salts thereof is 1:1.5, and wherein the veterinary composition produces a synergistic effect.

2. The method of claim 1, wherein the non-human mammal is a dog or a cat.

3. The method of claim 1, wherein the composition is intended for topical application.

4. The method of claim 1, wherein the composition is a spot-on, a pour-on, or a line-on composition.

5. A method for treating flea infestations in a non-human mammal, comprising administering to the non-human mammal a veterinary composition consisting essentially of an effective amount of dinotefuran or salts thereof and an effective amount of fipronil or salts thereof, wherein the ratio of dinotefuran or salts thereof to fipronil or salts thereof is 1:1.5, and wherein the veterinary composition produces a synergistic effect.

* * * * *

UNITED STATES PATENT AND TRADEMARK OFFICE
CERTIFICATE OF CORRECTION

PATENT NO. : 11,134,685 B2
APPLICATION NO. : 16/776303
DATED : October 5, 2021
INVENTOR(S) : Hamadi Karembe et al.

Page 1 of 1

It is certified that error appears in the above-identified patent and that said Letters Patent is hereby corrected as shown below:

In the Specification

At Column 5, Line 19, the text "methyl-2-nitro guanidine" should read --methyl-2-nitroguanidine--

At Column 14, Line 59, the text "EC5o" should read --ECso--

At Column 14, Line 64, the text "EC50" should read --ECso--

Signed and Sealed this
Twenty-third Day of August, 2022

Katherine Kelly Vidal
*Director of the United States Patent and Trademark Office*